(12) United States Patent
Spencer et al.

(10) Patent No.: US 6,871,052 B2
(45) Date of Patent: Mar. 22, 2005

(54) ANTENNA DIVERSITY RECEIVER

(75) Inventors: Adrian G. Spencer, Horley (GB); Robert J. Davies, Horley (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 797 days.

(21) Appl. No.: 09/894,098

(22) Filed: Jun. 28, 2001

(65) Prior Publication Data
US 2002/0004375 A1 Jan. 10, 2002

(30) Foreign Application Priority Data
Jul. 5, 2000 (GB) .............................................. 0016411

(51) Int. Cl.[7] ................................................. H04B 7/08
(52) U.S. Cl. .................... 455/226.2; 455/324; 455/132; 375/148; 375/349
(58) Field of Search ............................. 455/226.2, 324, 455/132, 133, 134, 41.2; 375/132, 136, 148, 349

(56) References Cited

U.S. PATENT DOCUMENTS 5,940,452 A  8/1999 Rich ........................... 375/347
6,014,571 A * 1/2000 Enoki ....................... 455/552.1
2003/0081656 A1 * 5/2003 Buehrer et al.

* cited by examiner

Primary Examiner—William J. Deane, Jr.

(57) ABSTRACT

An antenna diversity receiver comprises a zero-IF receiver connected to two antennas (102a, 102b) via switches (532, 534). Simultaneous measurement of signal qualities from both antennas is possible by routing signals from the first antenna (102a) via a first mixer (106) and channel filter (116) and routing signals from the second antenna (102b) via a second mixer (108) and channel filter (118). A diversity controller (536) compares the signal qualities received from the antennas (102a,102b) during a data preamble to select a preferred antenna, then adjusts the switches (532,534) to route the signals from the preferred antenna to both input mixers (106,108). The amplifier (104a,104b) connected to the deselected antenna may be switched off during data reception, thereby minimizing extra power consumption.

Such an antenna diversity receiver enables effective antenna selection to be performed, even in systems such as Bluetooth where only a very short preamble is provided for receiver configuration.

7 Claims, 2 Drawing Sheets

ANTENNA DIVERSITY RECEIVER

The present invention relates to an antenna diversity receiver for use in a radio communication system. Although the present invention is described with particular reference to a Bluetooth system, it is applicable to a range of other communication systems in which antenna diversity can be employed.

Radio communication systems often suffer from the effects of multipath propagation, whereby a transmitted signal reaches a receiver via a plurality of distinct paths from the transmitter. Each path (other than the direct path, if present) is reflected from one or more objects, and therefore the paths have different lengths. Signals from all available paths are recombined at an antenna and supplied to the receiver. Depending on the instantaneous set of path lengths, the received signals may interfere constructively or destructively at the antenna.

In the case of destructive interference, the instantaneous signal strength can be reduced by 20 dB or more compared with the signal strength of the direct path. This problem is particularly severe in systems for use indoors, where there is typically a wide range of scattering objects (for example walls, furniture, people) located close together, some of which are not static. In extreme cases the receiver cannot receive a signal of sufficient strength to use and is said to be in a null.

One solution to this problem is antenna diversity, in which two or more receiving antennas are provided for a receiver. Provided the antennas are sufficiently separated so that the signals received at one antenna are substantially uncorrelated with those received by another, when one antenna is in a null another antenna is likely to be able to receive a good signal.

An example of a radio communication system which may make use of antenna diversity is a Bluetooth network, operating according to the specification defined by the Bluetooth Special Interest Group. Such a network is intended to provide low-cost, short range radio links between mobile PCs, mobile phones and other devices, whether portable or not. Communication in a Bluetooth network takes place in the unlicensed ISM band at around 2.45 GHz. At such frequencies, antenna separations of the order of a few cm are sufficient for successful diversity operation.

In an antenna diversity receiver, for example that disclosed in U.S. Pat. No. 5,940,452, a diversity controller selects the antenna providing the best signal according to a signal quality measurement, which is most commonly the RSSI (Received Signal Strength Indication). Other measures of channel quality can be used, for example checksums are used in certain cases in a DECT (Digital Enhanced Cordless Telecommunications) system. In a radio communication system in which data is transmitted in packets, it is preferable for the diversity controller to select the optimum antenna on a packet-by-packet basis. This is particularly the case in a frequency-hopping system such as Bluetooth, because successive packets will be sent on different frequencies whose characteristics will not be correlated.

However, implementation of antenna diversity on a packet-by-packet basis requires measurement of the signal quality from each antenna in turn (unless a plurality of receivers is provided, which is not generally a practical solution). The sequential RSSI measurement process employed in known receivers may therefore take too long, particularly if the preamble to each packet is short (for example, that in Bluetooth is only 4 $\mu$s long).

An object of the present invention is to provide an antenna diversity receiver enabling simultaneous comparison of signal quality from two antennas without the need for a plurality of receivers.

According to the present invention there is provided an antenna diversity receiver comprising in-phase and quadrature channels, means for connection to first and second antennas, switching means having a first state in which signals from the first antenna are routed to the in-phase channel and signals from the second antenna are routed to the quadrature channel, a second state in which signals from the first antenna are routed to both in-phase and quadrature channels, and a third state in which signals from the second antenna are routed to both in-phase and quadrature channels, signal quality comparison means for determining the relative qualities of the received signals in the in-phase and quadrature channels when the switching means is in its first state, and diversity control means for controlling the state of the switching means depending on the relative signal qualities determined by the signal quality comparison means.

Embodiments of the present invention will now be described, by way of example, with reference to the accompanying drawings, wherein.

In the drawings the same reference numerals have been used to indicate corresponding features.

Figure 1:
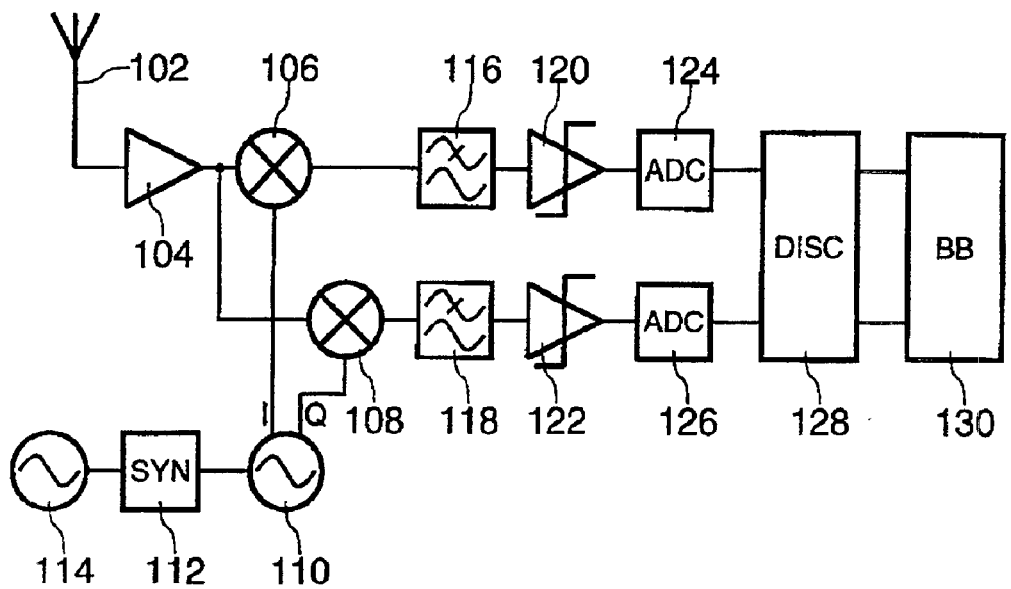
FIG. 1 is a block schematic diagram of a zero-IF radio receiver.
Figure 2:
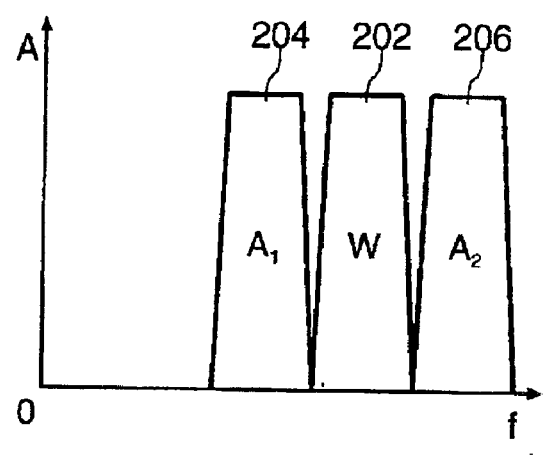
FIG. 2 is a graph of wanted and adjacent channel signals as received.

A block schematic diagram of a conventional zero-IF receiver is shown in FIG. 1. Its operation will be explained by reference to FIGS. 2 to 4, which are graphs showing signals as received and after processing in the receiver. Radio Frequency (RF) signals are received by an antenna 102 and amplified by a Low Noise Amplifier (LNA) 104. At this stage the RF signals are as shown in FIG. 2, which is a graph of the amplitude A of the signals against frequency f. A first frequency band 202 contains a wanted signal (W), while second and third frequency bands 204,206, contain unwanted adjacent channel signals $A_1$, $A_2$.

Figure 3:
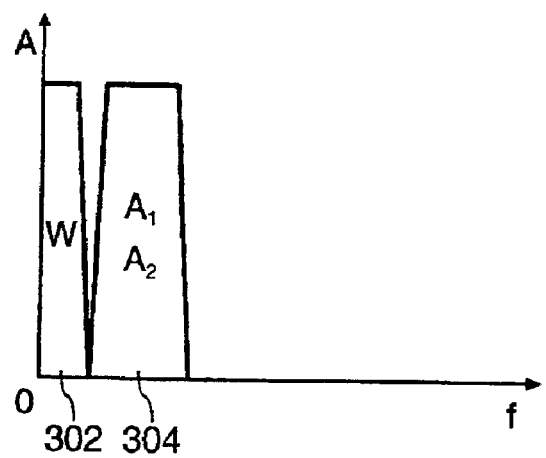
FIG. 3 is a graph of the signals of FIG. 2 mixing to zero IF.

The output of the LNA 104 is fed into a pair of quadrature-related mixers 106, 108, which are supplied with In-phase (I) and Quadrature (Q) Local Oscillator (LO) signals respectively. The LO signals are generated by a Voltage Controlled Oscillator (VCO) 110, driven by a frequency synthesiser (SYN) 112 having a stable reference signal source 114. The LO signals are at the same frequency as the centre of the frequency band 202 including the wanted signal, so the mixers 106,108 mix the signal to zero frequency, with the received spectrum folded around this frequency. The signals are now as shown in FIG. 3, with a lower frequency band 302 containing the wanted signal folded around zero frequency and an upper frequency band 304 containing the adjacent channel signals $A_1$ and $A_2$ superimposed.

Figure 4:
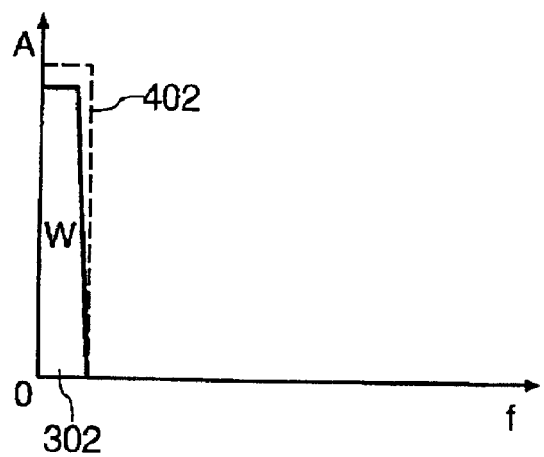
FIG. 4 is a graph of the signals of FIG. 3 after channel filtering.

The output signals from the I and Q mixers 106,108 are then filtered by low-pass I and Q channel filters 116,118, which attenuate the upper frequency band 304. FIG. 4 shows the resultant signals, with an idealised filter characteristic 402, shown as a dashed line, as a result of which the upper frequency band 304 has been removed. The output signals from the channel filters 116,118 are then passed through I and Q limiters 120,122 before being converted to digital signals by I and Q single-bit Analogue-to-Digital Converters (ADC) 124,126. The limiters 120,122 remove amplitude information prior to the inputs to the ADCs 124,126. The digital signals are then passed through a frequency discriminator (DISC) 128 to a BaseBand processing block (BB) 130 where they are demodulated. The effects of the spectrum folding can be removed by the baseband processing by use of the I and Q channels.

The receiver of FIG. 1 could be modified to operate with two antennas 102, to allow diversity switching, by adding a switch before the LNA 104 to allow the selection of signals from one of the antennas 102. An indication of the signal quality from each antenna 102 could then be derived sequentially, for example during a preamble in transmitted data. Once this measurement has been made, the antenna 102 providing the better signal, for example that with the higher RSSI, is selected.

Although such techniques have been used successfully, the fact that only one signal can be received at a time means that the measurement process takes a relatively long time. In a DECT system there is an optional provision for a prolonged preamble to enable such a measurement process to be completed. However, there is not sufficient time for such a measurement process in a system such as Bluetooth where the preamble is very short at only 4 μs. As an alternative it would be possible to have two separate receivers to enable simultaneous signal quality measurements, but such a receiver would not be economically viable.

Figure 5:
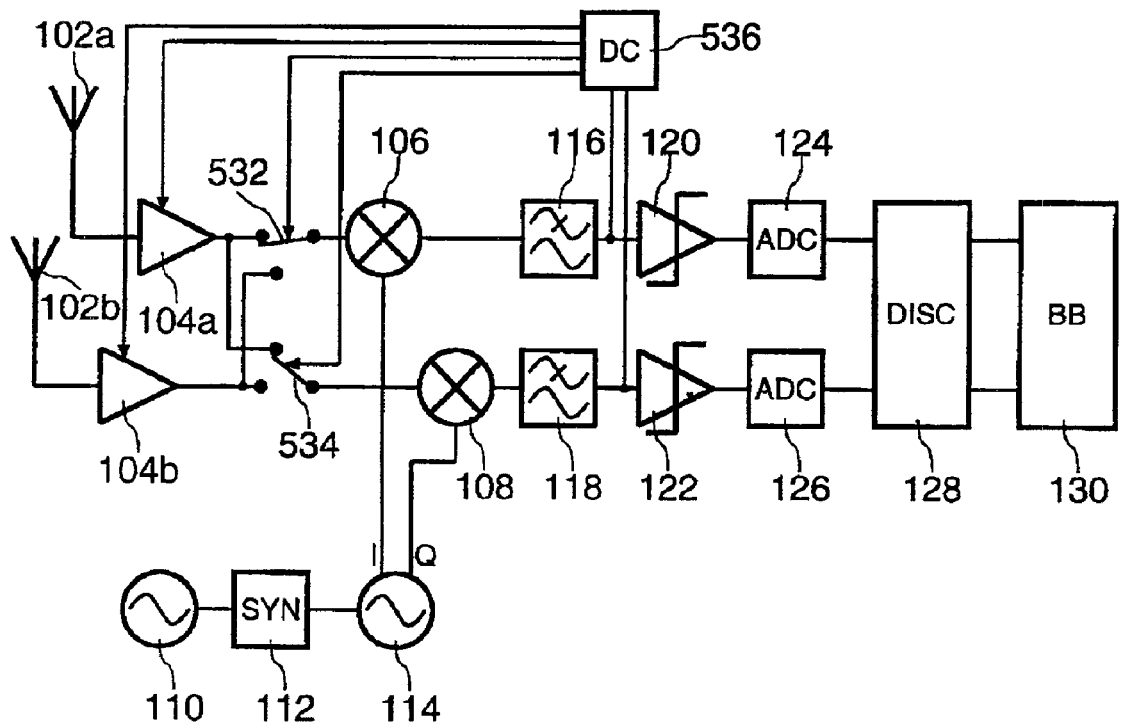
FIG. 5 is a block schematic diagram of an antenna diversity zero-IF radio receiver made in accordance with the present invention.

The present invention provides a solution to the problem of enabling simultaneous signal quality measurements with a single receiver. A block schematic diagram of a receiver made in accordance with the present invention is shown in FIG. 5. The majority of the receiver is identical to that of FIG. 1, and will therefore not be described again.

The receiver comprises first and second antennas 102a, 102b connected to respective first and second LNAs 104a, 104b. The outputs of the LNAs 104a,104b are connected to the quadrature-related mixers 106,108 via a first and second two-way switches 532,534. Additionally, a diversity controller (DC) 536 is provided which compares the received signal qualities and controls the switches 532,534 and LNAs 104a,104b accordingly. When both switches 532,534 are in the 'up' position, as shown in FIG. 5, the receiver behaves in the same way as the conventional zero-IF receiver shown in FIG. 1, receiving signals from the first antenna 102a. Similarly, when both switches 532,534 are in the 'down' position, signals are received from the second antenna 102b.

Simultaneous signal quality measurements (or comparisons) can be made when the first switch 532 is in the 'up' position and the second switch 534 is in the 'down' position. Signals from the first antenna 102a are fed to the I mixer 106, mixed down to zero frequency and filtered. The resultant signal is folded around zero frequency, as shown in FIG. 4, and therefore cannot be demodulated, but a valid signal strength measurement may still be taken. Similarly, signals from the second antenna 102b are fed to the Q mixer 108 and may have their strength measured after filtering. The fact that signals from the first antenna 102a are mixed with an in-phase LO signal and those from the second antenna 102b are mixed with a quadrature LO signal is of no consequence as it has no effect on the measured signal strength.

The diversity controller 536 is able to compare the signal qualities from the two antennas during a preamble in the transmitted data and to determine which antenna 102a,102b to use for the remainder of the data. When the decision has been taken it therefore sets the switches 532,534 accordingly and the receiver functions as a normal zero-IF receiver. The LNA 104a,104b connected to the unused antenna 102a,102b may be switched off during data reception, thereby minimising receiver power consumption.

Compared with a conventional zero-IF receiver, a receiver made in accordance with the present invention requires only a small amount of extra circuitry (one LNA and two switches in the illustrated embodiment) and makes only a small increase in the receiver's power consumption if the extra LNA is switched off during data reception as suggested above.

Variations on the receiver design shown in FIG. 5 are possible. For example, the limiters 120,122 could be removed and the single-bit ADCs 124,126 substituted by multi-bit ADCs, enabling signal strength measurements to be taken directly from the digital part of the receiver. The essential feature of a receiver made in accordance with the present invention is that two channels (normally I and Q) are required for normal operation, but each channel can be fed with a different signal during a period of signal quality measurement or comparison.

The embodiment disclosed above is a direct-conversion receiver, in which the RF signal is mixed down directly to zero frequency. However, the present invention is applicable to other zero-IF architectures such as those employing a two-stage down-conversion. It is also applicable to low-IF architectures employing a polyphase filter, although the implementation in such an architecture requires rather more additional circuitry. In particular, a signal would need to be derived from each of the I and Q channels between the mixers 106,108 and a polyphase filter replacing the channel filters 116,118 of FIG. 5. Each of these signals would then need to be passed through a separate channel filter, to filter out adjacent channel signals, before signal quality measurements could be made.

Although the present invention has been described in relation to a Bluetooth system or other systems having a very short preamble, simultaneous measurement of signal strengths from two antennas has significant advantages and could readily be applied to a wide range of radio communication systems, for example UMTS (Universal Mobile Telecommunication System), GSM (Global System for Mobile communications) or DECT.

From reading the present disclosure, other modifications will be apparent to persons skilled in the art. Such modifications may involve other features which are already known in the design, manufacture and use of antenna diversity receivers and component parts thereof, and which may be used instead of or in addition to features already described herein. Although claims have been formulated in this application to particular combinations of features, it should be understood that the scope of the disclosure of the present application also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention. The applicants hereby give notice that new claims may be formulated to such features and/or combinations of features during the prosecution of the present application or of any further application derived therefrom.

In the present specification and claims the word "a" or "an" preceding an element does not exclude the presence of a plurality of such elements. Further, the word "comprising" does not exclude the presence of other elements or steps than those listed.

What is claimed is:

1. An antenna diversity receiver comprising in-phase and quadrature channels, means for connection to first and second antennas, switching means having a first state in which signals from the first antenna are routed to the in-phase channel and signals front the second antenna are routed to the quadrature channel, a second state in which signals from the first antenna are routed to both in-phase and quadrature channels, and a third state in which signals from the second antenna are routed to both in-phase and quadrature channels, signal quality comparison means for determining the relative qualities of the received signals in the in-phase and quadrature channels when the switching means is in its first state, and diversity control means for controlling the state of the switching means depending on the relative signal qualities determined by the signal quality comparison means.

2. A receiver as claimed in claim 1, characterised in that the receiver is a zero-IF receiver.

3. A receiver as claimed in claim 1, characterised in that the signal quality comparison means includes means for determining a received signal strength indication for each signal.

4. A receiver as claimed in claim 1, characterised in that first and second amplifying means are provided for amplifying signals from a respective one of the first and second antennas, and in that the diversity control means includes means for switching off the amplifying means corresponding to the unused antenna when the switching means is in its second or third state.

5. An antenna diversity receiver implemented an integrated circuit, comprising in-phase and quadrature channels, means for connection to first and second antennas, switching means having a first state in which signals from the first antenna are routed to the in-phase channel and signals from the second antenna are routed to the quadrature channel, a second state in which signals from the first antenna are routed to both in-phase and quadrature channels, and a third state in which signals from the second antenna are routed to both in-phase and quadrature channels, signal quality comparison means for determining the relative qualities of the received signals in the in-phase and quadrature channels when the switching means is in its first state, and diversity control means for controlling the state of the switching means depending on the relative signal qualities determined by the signal quality comparison means.

6. A receiver as claimed in claim 5, characterised in that the signal quality comparison means includes means for determining a received signal strength indication for each signal.

7. A receiver as claimed in claim 5, characterised in that first and second amplifying means are provided for amplifying signals from a respective one of the first and second antennas, and in that the diversity control means includes means for switching off the amplifying means corresponding to the unused antenna when the switching means is in its second and third state.

* * * * *